United States Patent [19]
Mawhinney

[11] Patent Number: 5,394,882
[45] Date of Patent: Mar. 7, 1995

[54] PHYSIOLOGICAL MONITORING SYSTEM
[75] Inventor: Daniel D. Mawhinney, Livingston, N.J.
[73] Assignee: Respironics, Inc., Murrysville, Pa.
[21] Appl. No.: 95,290
[22] Filed: Jul. 21, 1993
[51] Int. Cl.$^6$ .............................................. A61B 5/08
[52] U.S. Cl. ..................................... 128/721; 128/671; 128/903
[58] Field of Search ............... 128/721, 723, 687, 782, 128/903, 670, 671; 607/149, 154, 156; 340/539, 573

[56] References Cited
U.S. PATENT DOCUMENTS

| | | | |
|---|---|---|---|
| 4,122,427 | 10/1978 | Karsh | 128/721 |
| 4,252,129 | 2/1981 | Tamura et al. | 128/903 |
| 4,638,808 | 1/1987 | Mawhinney | |
| 4,753,234 | 6/1988 | Mawhinney et al. | |
| 4,967,751 | 11/1990 | Sterzer | |
| 4,991,582 | 2/1991 | Mawhinney et al. | |
| 5,131,399 | 7/1992 | Sciarra | 128/903 |
| 5,220,922 | 6/1993 | Barany | 128/721 |

*Primary Examiner*—Lee S. Cohen
*Assistant Examiner*—Brian M. Green
*Attorney, Agent, or Firm*—Reed Smith Shaw & McClay

[57] ABSTRACT

A wireless monitoring system including at least one first unit for sensing motion and for directly radiating signals corresponding to the sensed motion. Additionally, the system includes a second unit for detecting signals radiated by the first unit and for converting the detected signals into electronic signals suitable for monitoring at compatible monitor apparatus.

15 Claims, 5 Drawing Sheets

PHYSIOLOGICAL MONITORING SYSTEM

FIELD OF THE INVENTION

The present invention relates in general to monitoring systems and, in particular, to systems which monitor physiological functions via detection of internal bodily motions. More particularly, the present invention provides a physiological sensor using directly radiated, motion induced oscillator frequency changes and a wireless telemetry system incorporating such a sensor.

BACKGROUND OF THE INVENTION

Most physiological functions, including breathing and heartbeat as well as other muscular actions, involve internal bodily motions that are uniquely related thereto. These motions include such actions as contraction of muscles, expansion of lungs, opening and closure of cardiac and other valves, and expansion and contraction of arteries in response to voluntary or involuntary physiological actions. Some of the larger scale of these internal motions, such as heart and respiratory functions, have heretofore been monitored by complicated equipment employing, inter alia, microwave or radio frequency Doppler radar systems. Systems of this kind are found in U.S. Pat. Nos. 4,638,808, 4,991,585, and 4,967,751.

In U.S. Pat. No. 4,638,808, for example, there is disclosed a microwave radar system capable of detecting a patient's heart rate. The system includes an antenna that is positionable adjacent a patient's thorax. The antenna both transmits microwave radiation into a patient's chest and receives therefrom Doppler shifted microwave signals representative of a combination of a patient's respiratory and cardiac activity. That component of the received signal which corresponds to respiration is extracted via a signal component separating circuit, whereby the ultimately displayed signal is reflective of the patient's heart rate.

U.S. Pat. No. 4,991,585 provides a triple antenna microwave radar system for measuring a patient's respiration and/or heartbeat. The triple antenna is placed adjacent a patient's thorax to transmit into and receive microwave radiation therefrom. One of the antennas is a microwave transmitter, a second is a microwave transducer and a third is a microwave receiver. Through elaborate circuitry the system processes microwave radiation reflected from objects both inside an outside of the patient's body, extracts spurious signals, and outputs a representative respiratory and/or heartbeat signal to an alarm-control means.

A related system is described in U.S. Pat. No. 4,967,751. According to this patent, however, a pair of cooperating microwave transducers are situated at opposite side s, i.e. front and back, of a patient's thorax to derive the desired heartbeat and/or respiratory signal. Although effective, the requirement of two transducer modules complicates design, manufacture and utilization of the system.

Some other physiological motions result in small, but significant, rearrangements of certain localized internal structure of the body. For example, periodic expansion of arteries responsive to blood flow is a motion indicative of a patient's pulse rate, a commonly monitored and important physiological function parameter. As with cardiac and respiratory activity, Doppler radar and other monitoring systems for pulse rate are also known.

In this connection, U.S. Pat. No. 4,753,243 discloses a pulse rate monitor comprising first and second units coupled by a cable. The first unit comprises, inter alia, a DC microwave oscillator and an antenna contained in a grounded case. In operation, the first unit preferably contacts the patient and is disposed at a desired location, e.g., with the antenna proximate an artery. The first unit is then activated to emit an oscillating DC signal. As the artery expands and contracts with each heart beat, the loading on the antenna and, therefore, the oscillator, changes. In turn, this causes the oscillating signal to be "pulled" into a pulsating signal in accordance with the pulse rate to be conveyed by the cable to the second unit. The second unit is typically connected to output means where the pulse rate signal can be seen and/or heard. While such a system enhances patient comfort through miniaturization of the first unit, the patient nonetheless remains encumbered by the potentially lengthy connector cable that is apt to become caught on bed rails, lavatory equipment, food trays, intravenous (IV) poles and other objects frequently encountered by a hospitalized patient. Consequently, either the first unit may become dislodged from the patient or the cable may disconnect from the second unit, thereby interrupting signal transmission.

An advantage exists, therefore, for a physiological sensor using directly radiated, motion induced oscillator frequency changes and a wireless telemetry system incorporating such a sensor.

SUMMARY OF THE INVENTION

Small movements of internal bodily tissue, bones, muscles, organs and cavities would present variable terminating impedance or load to an oscillating radiation source intimately coupled thereto. In the field of radio and microwave electronics, it is well known that the frequency of an oscillator is affected, to some degree, by the impedance or load to which it is coupled; see, for example, U.S. Pat. No. 4,753,243.

The present invention also proposes a physiological sensor which is attachable to a patient and comprises an oscillator whose frequency is influenced by internal bodily movements. Unlike that described in U.S. Pat. No. 4,753,243, however, the instant sensor operates as part of a completely wireless telemetry system for monitoring physiological function. That is to say, whereas the sensor oscillator of U.S. Pat. No. 4,753,243 is connected by cable to a receiving unit, the sensor oscillator of the present invention produces radiation which is detected by a remote receiver. More specifically, the oscillator frequency changes are monitored by a receiver tuned to the nominal frequency of the oscillator so as to detect leakage radiation therefrom.

An advantage of the present approach is that, without using any intermediate circuitry to convert the detected motions into electrically communicable signals, a radio frequency signal or the like is directly produced and radiated by the oscillator which corresponds to an internal motion related to a particular physiological function. A further advantage resulting from elimination of the sensor-to-receiver connecting cable is that signal transmission interruptions associated with snagging of the cable, e.g., dislodgement of the sensors ad disconnection of the cable, are likewise eliminated.

Further, minimal circuitry is borne by the individual; it is only necessary to attach an oscillator with a coupling structure, such as a matched antenna and a small battery, to sense the desired motion. Accordingly, discomfort and inconvenience are virtually eliminated because of the light weight of such a construction and also because the subject is free to move about without fear of snagging any cables on projecting surfaces and objects. Moreover, the remote receiver can be constructed to be capable of detecting the leakage signals from a plurality of the sensors, if such is desired or necessary.

Other details, objects and advantages of the present invention will become apparent as the following description of the presently preferred embodiments and presently preferred methods of practicing the invention proceeds.

FIG. 2A is a circuit diagram of an alternative wireless sensor adapted for use in the physiological monitoring system of the present invention.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE INVENTION

The wireless monitoring system of the instant invention includes as an essential component at least one first unit means for sensing motion and for directly radiating signals corresponding to the sensed motion. Additionally, the system includes second unit means, to be described in greater detail hereinafter, for detecting signals radiated by the first unit means and for converting the detected signals into electronic signals suitable for monitoring at compatible output means.

Figure 1:
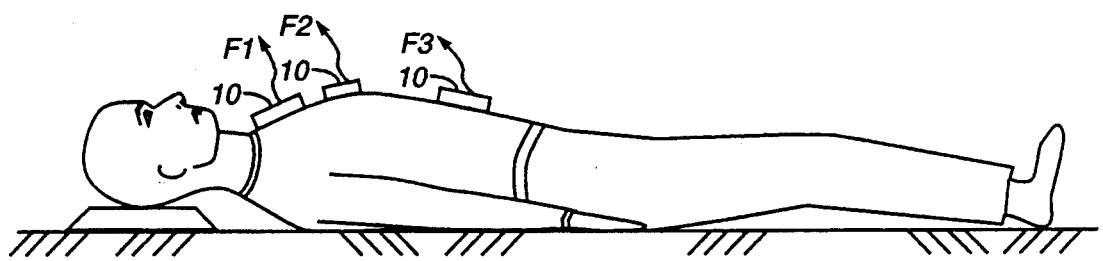
FIG. 1 depicts a typical placement of a plurality of wireless sensors of the present invention onto the thorax of a subject.

With reference to FIG. 1, there is shown a plurality of the first unit means, herein designated by reference numeral 10, in contact with the subject individual at desired locations whereat internal bodily motions corresponding to physiological functions of interest are to be monitored. Although not necessary to obtain a sufficient signal, the first unit means 10 are preferably attached to the individual by bio-compatible non-allergic adhesive or tape to eliminate relative motion therebetween. In the illustrated arrangement, the first unit means 10 are disposed generally at the subject's throat, chest and abdomen and respectively radiate electromagnetic radiation at frequencies F1, F2 and F3. It will be understood that although three first unit means 10 are shown, less than three (even as few as one) and greater than three such means may be employed, as desired, to achieve the objects of the invention. Moreover, the first unit means 10 may be situated at other locations and may be appropriately adapted to sense internal bodily motions associated with cardiac activity, respiratory activity and pulse rate, among others.

Figure 2:
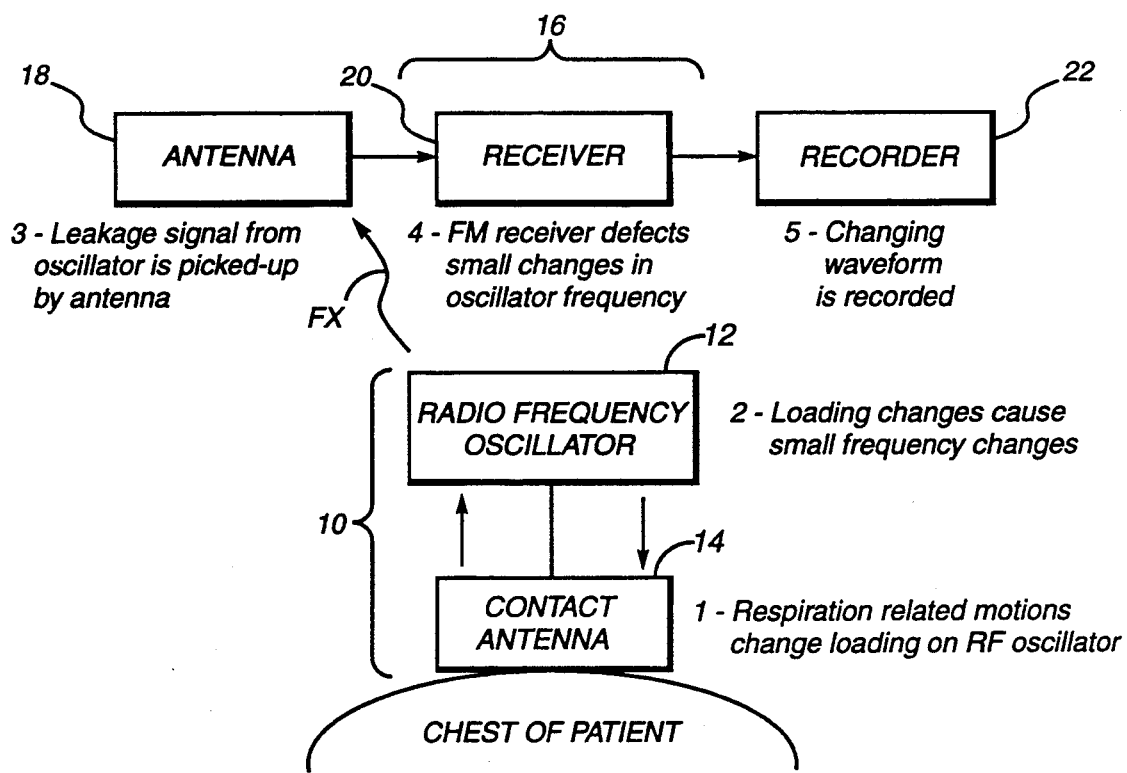
FIG. 2 is a schematic flow diagram representing the operation of the physiological monitoring system of the present invention.

Each first unit means 10 is a wireless sensor and comprises an oscillator 12 and an antenna 14 as schematically depicted in FIG. 2. The specifics of a presently preferred construction of the first unit means will be described later herein in respect to FIGS. 5, 6, 7A, 7B, 7C, 7D, 8A and 8B. Furthermore, each first unit means also includes an DC power source. In this regard, good results may be accomplished by one or more on-board, miniaturized lithium batteries. As will be appreciated, the first unit means may also include an ON-OFF switch or may be activated simply by installing the batteries whereby its operation would be continuous until the batteries were removed or their power supply was depleted. Moreover, the first unit means 10 may also include a low power amplifier to provide a more powerful leakage signal to second unit means, as will be described in somewhat greater detail later herein.

The basic operation of the monitoring system is sequentially represented in FIG. 2. Initially, the first unit means 10 is disposed at the desired location, e.g., the chest, of the subject whereat the antenna 14 can be optimally influenced by the internal bodily tissue movement to be monitored. The first unit means are then activated whereby the oscillator 12 commences oscillation. Any suitable low power oscillator including, but not limited to, a tunable microwave or ultrasonic oscillator may be employed in first unit means 10. A presently preferred embodiment employs a radio frequency (RF) oscillator, namely a Murata 915 MHz, Model No. 915-5 VCO.

As is known, any oscillator has an inherent tendency to change frequency or "pull" as the output loading thereof is changed. Such a loading change is related to the impedance change and load stability (Qx) of the oscillator. In the present system a loading change sufficient to cause oscillator 12 to pull will occur when the antenna couples the oscillator output to the internal bodily movements of the subject, e.g., the displacements of muscles and organs relative to the antenna 14 during respiration. Hence, as the target bodily tissues move with respect to the antenna, the pattern of the movement is reflected in the frequency change of the oscillator. Further, certain internal bodily movements possess readily identifiable patterns associated with their physiological function, which patterns may vary in frequency and/or amplitude but not substantially in general configuration. Examples of categorizable bodily tissue movement patterns include the reciprocating and undulating motions associated with respiration, the pulsation of an artery expanding and contracting with each heart beat, and the multiple spiked pattern indicative of the opening and closing of the various chambers of the heart. In many cases, the waveform will only show the existence of motion but not its character, although rate of the motion even if inconsistent, will be accurately reflected. Thus, a single oscillator may be influenced by a number of these bodily movements to produce composite waveform signals which, through appropriate filtering at a remote second unit means 16 described below, can be converted into one or electronic signals suitable for monitoring. Alternatively, a plurality of the first unit means 10 can be strategically placed about the subject's body whereby the oscillators thereof can be focussed on a specific bodily activity with reduced interference from other internal movements.

In the example shown in FIG. 2, respiration related movements change the loading on the RF oscillator 12. These loading changes in turn cause small frequency changes in the oscillator. A leakage signal FX from the antenna 14 of first unit means 10 reflecting the influenced oscillator signal is detected by an antenna 18.

Figure 2A:
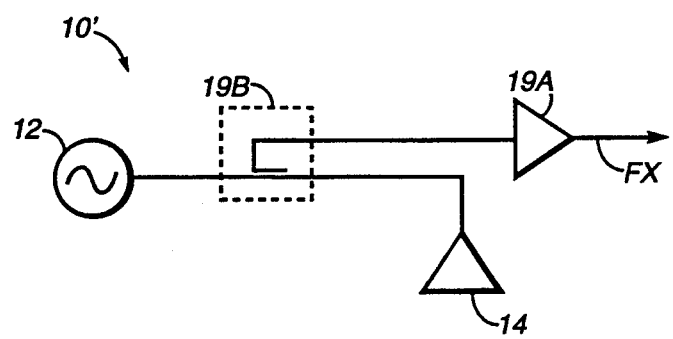
FIG. 2A is a circuit diagram of a wireless sensor adapted for use in the physiological monitoring system of the present invention.

An amplifier may be provided to increase the output level of the leakage signal FX without causing the first unit means to be materially more susceptible to frequency "pulling" by external motions. In this connection, and as shown in FIG. 2A, a further embodiment of the first unit means circuit includes an amplifier 19A lightly coupled by a directional coupler 19B to the oscillator 12, thereby boosting leakage signal FX with oscillator performance remaining substantially unaffected.

The second unit means 16 comprises a receiver 20, the circuitry of exemplary embodiments of which is described below in connection with the discussion of FIGS. 3 and 3A. The receiver 20, suitably an FM receiver attuned to the nominal frequency of the oscillator(s) 12, is fed the leakage signal detected by antenna 18 and processes the signal to produce one or more monitorable output signals- which reflect changes in the nominal frequency of the oscillator(s). The output signals are then transmitted to an output means or recorder(s) 22 such as, for example, one or more oscilloscope and/or audio amplifiers and loudspeakers where the signals can be seen and/or heard. It is contemplated that the recorder(s) 22 may be either housed within or be separated from the second unit means 16 depending upon the manner in which the subject is to be monitored, e.g., locally or remotely. Likewise, the antenna 18 may also be housed within, detachably or adjustably connected to, or tethered by cable and freely positionable relative to the second unit means 16 to effectuate optimum leakage radiation detection. That is, the second unit means may also comprise the recorder(s) 22 and/or the antenna 18 depending upon operational needs.

Figure 3:
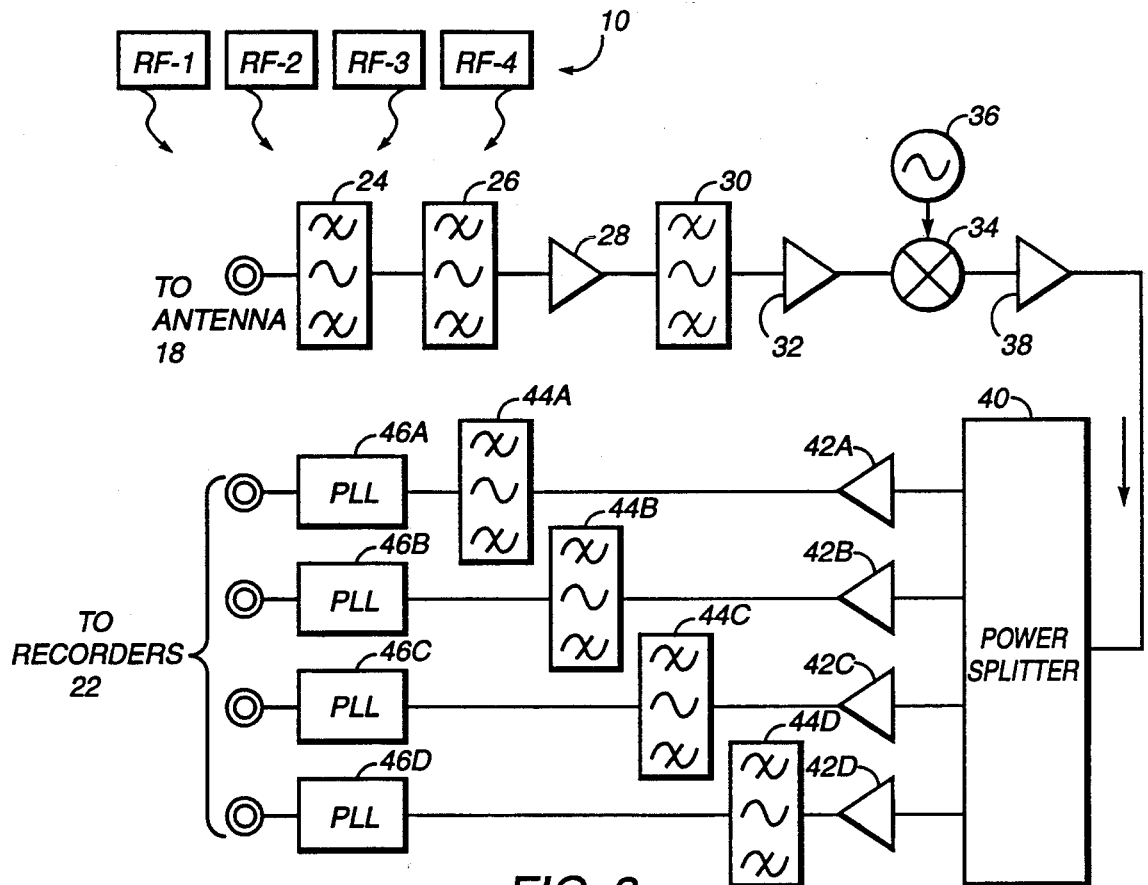
FIG. 3 is a schematic diagram illustrating a receiver circuit adapted to monitor up to four wireless sensors.

Referring to FIG. 3, an illustrative example of the circuitry of the receiver 20 of the second unit means 16 is provided. In the example, four wireless sensors or first unit means 10 are attached to a subject and radiate internal bodily movement influenced oscillation signals which are detected by antenna 18. Because of the relatively wide range of the preferred Murata 915 MHz, Model No. 915-5 VCO, the oscillators of the first unit means 10 can be accurately tuned to four distinct nominal radio frequencies, i.e., RF-1, RF-2, RF-3 and RF-4 such that the frequency variation between each nominal frequency may be as high as 10 MHz.

The signals from the antenna 18 are communicated to the receiver 20 where out-of-band signals are filtered by low-pass (LP) filter 24 and a high-pass (HP) filter 26. The RF signals of proper band are then amplified at amplifier 28 and more sharply filtered by a narrowband, bandpass (BP) filter 30, reamplified at amplifier 32 and then fed to a first input of a mixer 34. Mixer 34 is preferably a double-balanced mixer a second input of which is connected to and receives a modulation signal from a local carrier frequency oscillator 36. Preferably, local oscillator 36 is an RFM 915 MHz SAW oscillator. The signals are downconverted in mixer 34 to an intermediate frequency in the range of about 10 to 30 MHz and then output to an intermediate frequency (IF) amplifier 38 whereat the signals are amplified and transmitted to power splitter 40. The power splitter splits and transmits the signals into four paths depending upon the requirements of the IF amplifiers 42A, 42B, 42C and 42D. From these amplifiers, the split and amplified signals pass respective IF BP filters 44A, 44B, 44C and 44D and thereafter used to lock phase locked loop (PLL) oscillators 46A, 46B, 46C and 46D that operate as frequency discrimination means for producing monitorable signals indicative of selected physiological function(s). The output from the PLL oscillators 46A-46D is communicable with the output means 22, i.e., the recorders, where the changing frequency or FM components of the signals are converted into DC voltages representing the motion of the bodily tissue that can be visually and/or audibly monitored.

Figure 3A:
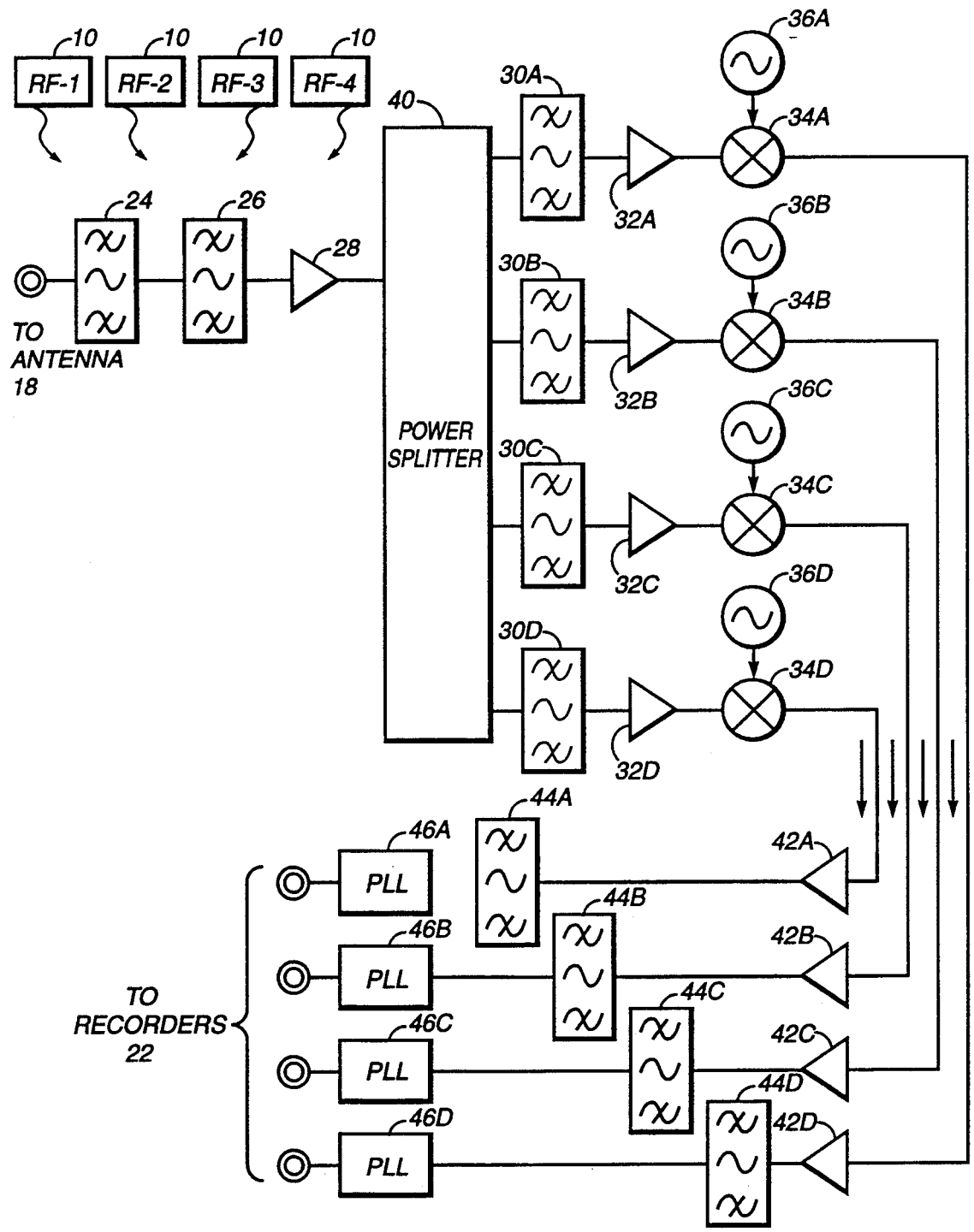
FIG. 3A is a schematic diagram of an alternative receiver circuit.

FIG. 3A reveals a further preferred embodiment of the signal receiving circuitry of second unit means 20. Like references in this figure represent elements similar to those thus far discussed in respect to the circuitry of FIG. 3. Further, the receiving circuitry of FIG. 3A operates much like that of FIG. 3; hence, only those aspects which measurably depart from the circuitry of FIG. 3 will be described in detail, except where otherwise necessary for purposes of clarity.

According to this embodiment, the power splitter 40 immediately follows amplifier 28. The power splitter splits and transmits the signal from amplifier 28 into four paths whose individual signals are more sharply filtered by bandpass filters 30A, 30B, 30C and 30D which are selected to satisfy the requirements of respective preamplifiers 32A, 32B, 32C and 32D. The signals from these preamplifiers are then respectively fed to first imputs of mixers 34A, 34B, 34C and 34D. Like mixer 34 of FIG. 3, mixers 34A-34D are desirably double-balanced mixers the second inputs of which are connected to and receive modulation signals from local carrier frequency oscillators 36A, 36B, 36C and 36D, respectively. Preferably, oscillators 36A-36D are RFM 915 MHz SAW oscillators, although other oscillators having suitable operational characteristics would be acceptable for this purpose. The signals from preamplifiers 32A-32D and local oscillators 36A-36D are converted in mixers 34A-34D to discrete intermediate frequencies in the range of about 10 to 30 MHz and then output to intermediate frequency (IF) amplifiers 42A-42D. From amplifiers 42A-42D signal processing continues in the manner described above with respect to FIG. 3. Advantages of the receiver circuitry configuration of FIG. 3A include more effective use of oscillator discriminator ranges of phase locked loops (PLLs) 46A-46D and increased isolation of one sensor from another, hence resulting in high-clarity, low-interference signals being transmitted to output means 22.

It will be appreciated that the circuitry illustrated in FIGS. 3 and 3A can be used to process the physiological functions monitored by less than four first unit means 10. Similarly, circuits specifically adapted for monitoring fewer (or greater) than four first unit means 10 but containing the appropriately configured essential components, or their equivalents, of the circuitry of FIGS. 3 and 3A are also considered to be within the scope of the present invention.

Figure 4A:
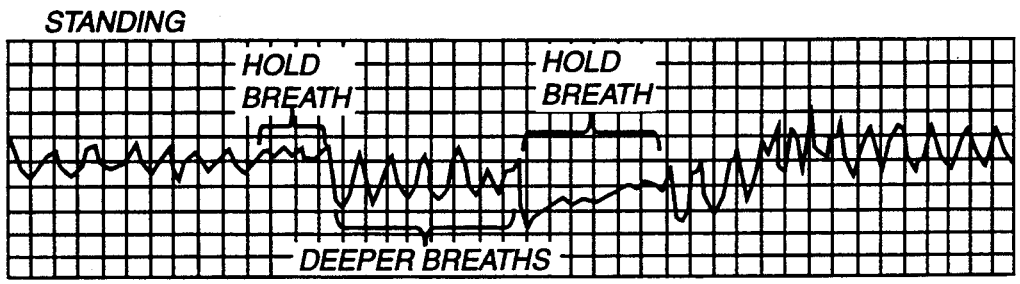
FIGS. 4A and 4B show actual waveforms using the circuit shown in FIG. 3 and demonstrating various respiration patterns as influenced by a subject's body position.
Figure 4B:
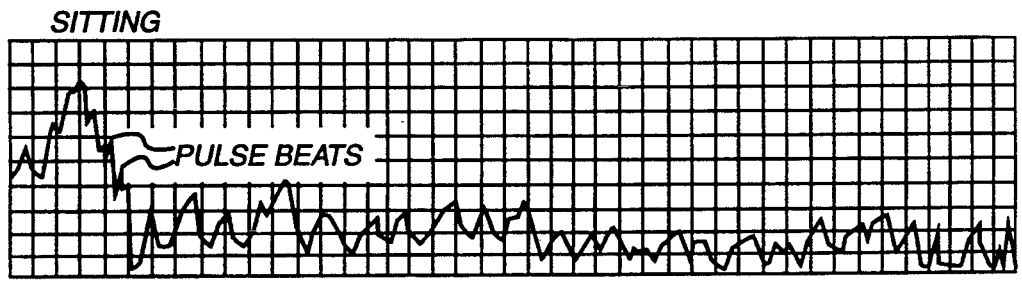

FIG. 4A is a strip chart recording of the respiratory activity of a subject in a standing position and fitted with one wireless sensor 10 situated generally below the neck approximately at the top of the sternum. The signals radiated by the sensor were detected and processed by second unit means including a receiver 20 having the circuitry of FIG. 3. Periods where the subject held his breath and breathed deeply are identified. FIG. 4B is a strip chart of the same individual in a sitting position (with the subject's heart pulse beats being identified in addition to his respiratory waveform). In both figures, the subject's monitored waveform assumes the expected sinusoidal waveform of respiratory activity, the frequency and amplitude of which varies according to, inter alia, the user's activity and body position. With proper signal processing and filtering, as evinced by FIG. 4B, both respiration and heartbeat can be independently monitored and measured from the same wireless sensor.

Figure 5:
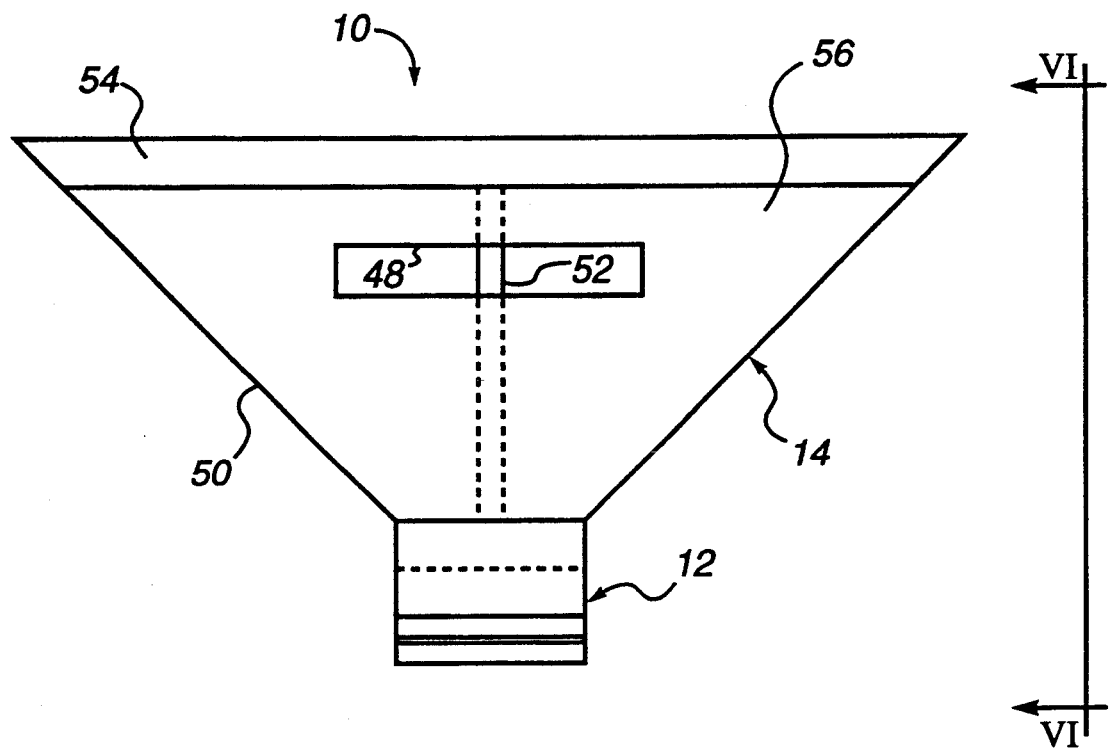
FIG. 5 is a plan view of a wireless sensor constructed according to the present invention.
Figure 6:
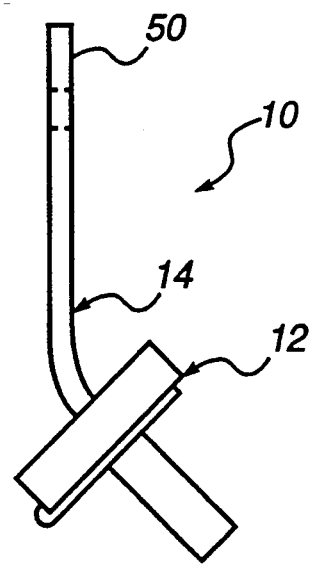
FIG. 6 is a view taken along line VI—VI of FIG. 5.

FIGS. 5 and 6 reveal a first presently preferred construction of the first unit means 10. The oscillator (including batteries) is generally designated by reference numeral 12, the antenna by reference numeral 14. It will be understood that, although not shown, there may also be included in this construction an amplifier 19 and directional coupler 19B to boost leakage signal strength in accordance with that discussed hereinabove with reference to first unit means of FIG. 2A. This present embodiment employs a construction known as a slot antenna, having a slot 48 provided in a substrate 50. The substrate is desirably 0.025" thick E-10 flexible softboard material or the like having a slot size of approximately 1.80"×0.20". A feedline 52 is connected to the oscillator 12 and crosses the slot 48 at the surface opposite surface 56. The end of the feedline opposite the oscillator is shorted by suitable means such as shorting tape 54. Surface 56 may be coated with any conventional bio-compatible, non-allergenic adhesive to enable attachment of the first unit means 10 to the subject. Alternatively, the unit may be attached by adhesive tape.

Further embodiments of the first unit means are depicted in FIGS. 7A, 7B, 7C, 7D, 8A and 8B. Again, although not illustrated, each of the following descriptions of the first unit means can be provided with an amplifier and associated directional coupler, if desired.

Figure 7A:
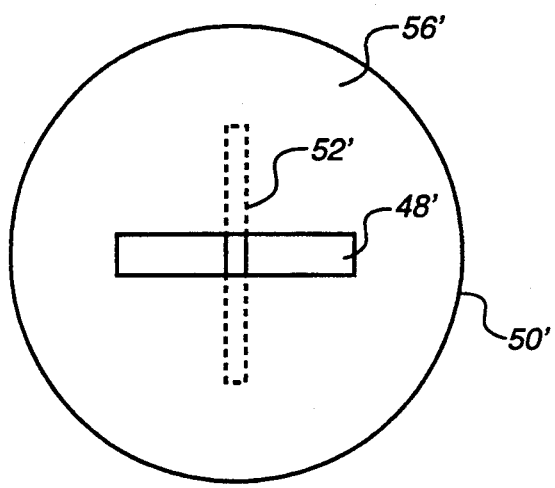
FIG. 7A is a front view of an antenna adapted for use in a wireless sensor according to the present invention.
Figure 7B:
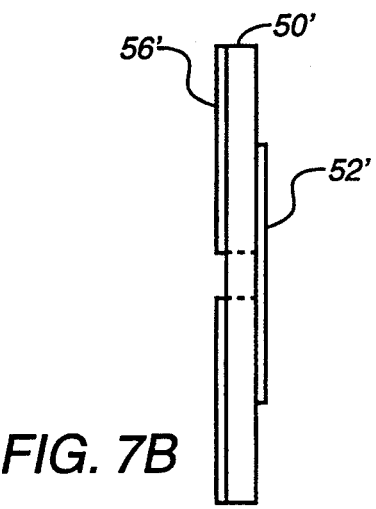
FIG. 7B is a side view of the antenna shown in FIG. 7A.

Revealed in FIGS. 7A and 7B is a first embodiment of a disc-shaped antenna including substrate 50' which may be formed of any suitable flexible, semi-rigid or rigid dielectric material. Substrate 50' is provided with a metalized surface 56' having formed therein a substantially rectangular etched slot 48' which exposes the dielectric. The opposite surface of the substrate carries a feedline 52' extending in a direction crossing slot 48'.

Figure 7C:
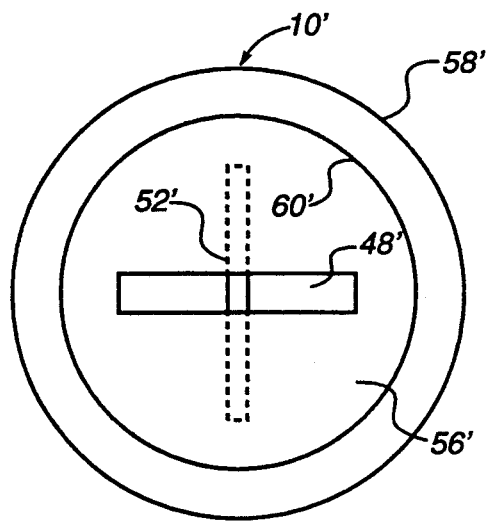
FIG. 7C is a front view of the antenna of FIGS. 7A and 7B installed in a wireless sensor according to the present invention.
Figure 7D:
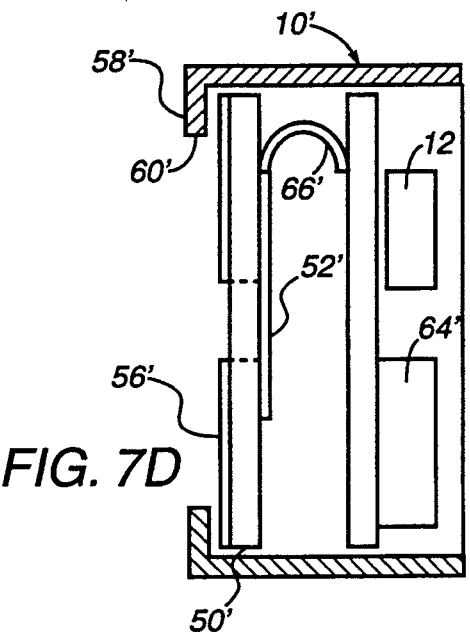
FIG. 7D is a side view, in partial section of the antenna of FIGS. 7A and 7B installed in a wireless sensor according to the present invention.

FIGS. 7C and 7D illustrate the antenna incorporated into a complete first unit means, herein designated by reference numeral 10'. In accordance with this embodiment, the antenna is enclosed within a housing 58' including an opening 60' exposing metallized surface 56'. Housing 58' is desirably formed of metal and contains an internal board 52' to which it is electrically connected. Board 52' electrically links an RF oscillator 12 with a battery 64'. A coaxial cable 66' or other suitable connector provides electrical communication between the feedline 52 and the battery/oscillator circuit. The metallized surface 56' serves as the contact antenna and may be coated with bio-compatible, non-allegenic adhesive for enabling adhesive attachment of the first unit means 10' to the subject.

Figure 8A:
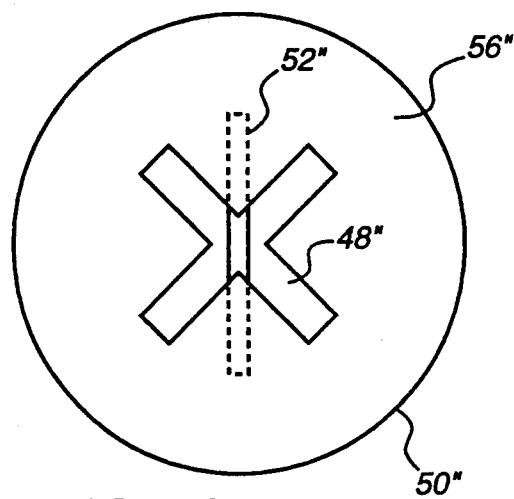
FIG. 8A is a front view of an alternative antenna adapted for use in a wireless sensor according to the present invention.
Figure 8B:
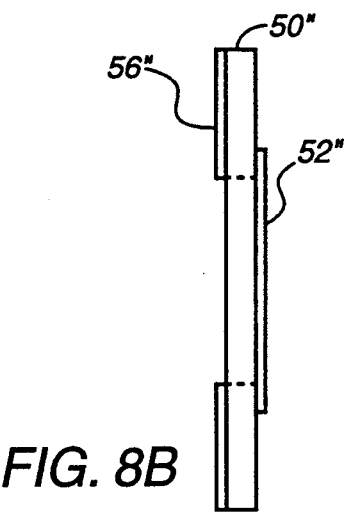
FIG. 8B is a side view of the antenna shown in FIG. 8A.

As to FIGS. 8A and 8B, the disc-shaped antenna whose components are identified by double prime (")numerals is substantially identical to the antenna shown in FIGS. 7A-7D and may be incorporated into a housing similar to housing 58'. However, in this embodiment, slot 48" is substantially X− or +-shaped. An advantage to such a slot design is that, under certain circumstances, it may provide a better match to the subject. Moreover, it can be significantly less susceptible to specious or unintended motion detection, as well as the inability to detect the desired motion, which may arise from imprecise placement of the first unit means on the subject.

The novel system and technique herein disclosed is not limited merely to the motions produced by physiological function. Any volumetric change or motion of materials sufficiently close to or coupled to the first unit means 10 so as to produce frequency changes that exceed the inherent instability or FM noise of the oscillator 12 can be monitored in the same manner. This technique may be applicable to "paste-on" industrial or security sensors that can be monitored by a single remote receiver. The invention also does not preclude use of wires to connect the first unit means to a power source other than an included battery or with more complex directional antennas to detect motions at a substantial distances. For instance, the physiological monitoring approach propounded herein could also be used for extremely remote monitoring of people, animals, or moving objects by using a directional receiving antenna and a sensitive receiver. Patients would be "wirelessly" monitored during procedures, e.g., operations, from receivers mounted on ceilings or wall, etc., or, alternatively, for wireless "stress" monitoring, and the like.

Although the invention has been described in detail for the purpose of illustration, it is to be understood that such detail is solely for ! 2hat purpose and that variations can be made therein by those skilled in the art without departing from the spirit and scope of the invention except as it may be limited by the claims.

What is claimed is:

1. A wireless system for monitoring motion associated with a subject, said system comprising:
   at least one first unit means for generating and radiating signals corresponding to said motion, said first unit means having an oscillator adapted to be operably coupled to said subject and means for supplying a current to said oscillator, said oscillator including means to draw supply current in accordance with subject loading thereon associated with said motion and to generate signals corresponding to said motion responsive to said subject loading; and a second unit means remote from said first unit means for receiving aid radiated signals and for converting said radiated signals into at least one signal suitable for monitoring.

2. The system of claim 1 wherein said at least one first unit means include a plurality of said first unit means.

3. The system of claim 1 wherein said current is DC current.

4. The system of claim 3 wherein said first unit means further comprises an antenna connected to said oscillator and operable to transmit said radiated signals.

5. The system of claim 4 further comprising means for attaching said first unit means to said subject.

6. The system of claim 5 wherein said attaching means is a bio-compatible, non-allergenic adhesive.

7. The system of claim wherein said oscillator is a radio frequency oscillator.

8. The system of claim 1 wherein said second unit means comprises an antenna for detecting said radiated signals.

9. The system of claim 8 wherein said second unit means further comprises an output means for enabling monitoring of said at least one signal suitable for monitoring.

10. A wireless system for monitoring motion associated with a subject, said system comprising:

at least one first unit means for generating and radiating signals corresponding to said motion, said first unit means having an oscillator adapted to be operably coupled to said subject and means for supplying a current to said oscillator, said oscillator including means to draw supply current in accordance with subject loading thereon associated with said motion and to generate signals corresponding to said motion responsive to said subject loading wherein said motion is at least one physiological motion and said radiated signals are signals corresponding to physiological activity associated with said at least one physiological motion; and a second unit means remote from said first unit means for receiving said radiated signals and for converting said radiated signals into at least one signal suitable for monitoring.

11. A wireless sensor for monitoring motion associated with a subject, said sensor comprising:

an oscillator adapted to be operably coupled to said subject and means for supplying a current to said oscillator, said oscillator including means to draw supply current in accordance with subject loading thereon associated with said motion and to generate signals corresponding to said motion responsive to said subject loading; and antenna means connected to said oscillator for radiating said generated signals corresponding to said motion.

12. The sensor of claim 11 wherein said current is DC current.

13. The sensor of claim 11 further comprising means for attaching said sensor to said subject.

14. The sensor of claim 13 wherein said attaching means is a bio-compatible, non-allergenic adhesive.

15. The sensor of claim 11 wherein said oscillator is a radio frequency oscillator.

* * * * *